United States Patent [19]

Franczyk et al.

[11] Patent Number: 5,739,390
[45] Date of Patent: Apr. 14, 1998

[54] PROCESS TO PREPARE AMINO CARBOXYLIC ACID SALTS

[75] Inventors: Thaddeus Stephen Franczyk, St. Louis, Mo.; Yukio Kadono, Kawasaki, Japan; Norikazu Miyagawa, Kawaguchi, Japan; Seiji Takasaki, Kawagoe, Japan; Hiroki Wakayama, Kawasaki, Japan

[73] Assignee: Monsanto Company, St. Louis, Mo.

[21] Appl. No.: 532,624

[22] PCT Filed: Apr. 6, 1994

[86] PCT No.: PCT/US94/03770

§ 371 Date: Jan. 16, 1996

§ 102(e) Date: Jan. 16, 1996

[87] PCT Pub. No.: WO94/24091

PCT Pub. Date: Oct. 27, 1994

Related U.S. Application Data

[63] Continuation-in-part of Ser. No. 44,682, Apr. 12, 1993, Pat. No. 5,292,936.

[30] Foreign Application Priority Data

May 14, 1993 [JP] Japan ................................ 5-113127
Sep. 20, 1993 [JP] Japan ................................ 5-233622

[51] Int. Cl.$^6$ .................................................. C07C 51/23
[52] U.S. Cl. ............................................ 562/526; 502/103
[58] Field of Search ................................. 562/539, 526, 562/103; 502/103

[56] References Cited

U.S. PATENT DOCUMENTS

| | | |
|---|---|---|
| 3,864,369 | 2/1975 | Isa et al. . |
| 4,782,183 | 11/1988 | Goto et al. . |
| 4,810,426 | 3/1989 | Fields, Jr. et al. . |
| 4,847,013 | 7/1989 | Müller . |
| 5,220,054 | 6/1993 | Urano .................................. 562/539 |
| 5,292,936 | 3/1994 | Franczyk ............................ 562/526 |

FOREIGN PATENT DOCUMENTS

WO 92/06069   4/1992   WIPO .

OTHER PUBLICATIONS

"Structure and Activity of Chromiun–Promoted Raney Copper Catalyst for Carbon Monoxide Oxidation", Laine et al., *Applied Catalysis*, 44 (1–2), pp. 11–22, 1988.

*Primary Examiner*—C. Warren Ivy
*Assistant Examiner*—Jean F. Vollano
*Attorney, Agent, or Firm*—James M. Warner; Arnold, White & Durkee

[57] ABSTRACT

An improved process is discloses to prepare an amino carboxylic acid salt. According to the process an aqueous solution of an amino alcohol is contacted with an alkali metal hydroxide in the presence of an effective amount of Raney copper catalyst that has from about 10 parts per million of an element selected from the group consisting of bismuth, tin, antimony, lead, germanium and mixtures thereof.

11 Claims, No Drawings

PROCESS TO PREPARE AMINO CARBOXYLIC ACID SALTS

CROSS REFERENCE TO RELATED APPLICATIONS

This application is a 371 of PCT/US94/03770 filed Apr. 6, 1994 which is a continuation-in-part of U.S. patent application Ser. No. 08/044,682 filed Apr. 12, 1993, now U.S. Pat. No. 5,292,936.

BACKGROUND OF THE INVENTION

This invention relates to the preparation of amino carboxylic acid salts, and more particularly, relates to a method for the preparation of amino carboxylic acid salts by the reaction of amino alcohols with an alkali metal hydroxide in the presence of a copper catalyst.

Amino carboxylic acid salts are useful in various applications. The glycine salt, for example, can be neutralized to glycine, which is widely used as an additive in processed meat, beverages, and in other processed food stuffs. It is also used widely as a raw material for pharmaceuticals, agricultural chemicals and pesticides. Iminodiacetic acid salt can be neutralized to iminodiacetic acid, and is used in various applications such as a raw material for the preparation of agricultural chemicals and pharmaceuticals. The nitrilotriacetic acid salt is useful as a detergent builder. Other amino carboxylic acids that can be prepared by the process of the present invention have useful applications.

U.S. Pat. No. 4,782,183 to Goto et al. discloses a method for the manufacture of amino carboxylic acid salts which comprises subjecting an amino alcohol to an alkali metal hydroxide in the presence of a Raney copper catalyst.

In a patent application published by WIPO as WO 92/06069 on Apr. 16, 1992, a process is disclosed for producing glycine, iminodiacetic acid and nitrilotriacetic acid salts by contacting monoethanolamine, diethanolamine or triethanolamine with an alkali metal hydroxide in the presence of a Raney copper catalyst, wherein at least some of the Raney copper catalyst has been rejuvenated by treating the catalyst under reflux conditions with formic acid (attorney docket No. 39-21(3145)).

A journal article "Structure and Activity of Chromium-Promoted Raney Copper Catalyst for Carbon Monoxide Oxidation" by Laine et al., Applied Catalysis, 44 (1-2), pages 11-22, discloses that chromium-promoted Raney copper catalysts were prepared, and their activity for the oxidation of carbon monoxide was measured. The surface area of the Raney copper catalyst was directly related to the aluminum content in the precursor alloy and to a lesser extent to the presence of chromium. Bulk cuprous oxide and cupric oxide were detected by X-ray diffraction in the Raney copper catalyst. The presence of chromium inhibited the formation of cupric oxide but not of cuprous oxide. The activity decreased as chromium content increased.

U.S. Pat. No. 4,810,426 to Fields et al., discloses a process for the production of N-phosphonomethylglycine by oxidizing N-phosphonomethylethanolamine or the cyclic internal ester thereof with an excess of an aqueous alkali and a copper catalyst, and thereafter heating at a temperature between 200° and 300° C. Thereafter, the salt is neutralized with an acid to produce the desired N-phosphonomethylglycine.

Although satisfactory results are achieved by the processes of the prior art to convert an amino alcohol to a amino acid using a copper catalyst, or even a Raney copper catalyst, it has been found that upon repeated usage of the copper catalyst, the activity of the catalyst decreases. Now, it has been found, in accordance with the teachings of the present invention, that the activity of the copper catalyst can be extended to a significant degree, permitting more economic utilization of the catalyst.

SUMMARY OF THE INVENTION

These and other advantages are achieved in a process to manufacture an amino carboxylic acid salt which comprises contacting an aqueous solution of an amino alcohol represented by the formula:

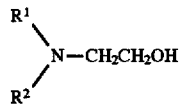

wherein $R^1$ and $R^2$ are individually selected from the group consisting of hydrogen, a hydroxyethyl group, —$CH_2COOH$, an alkyl group having from 1 to 18 carbon atoms, an aminoalkyl group having 2 to 3 carbon atoms, a hydroxyalkylaminoalkyl group having 2 to 3 carbon atoms, and phosphonomethyl; with an alkali metal hydroxide in the presence of an effective amount of a copper catalyst containing from about 10 parts per million to about 50,000 parts per million of an element selected from the group consisting of chromium, titanium, niobium, tantalum, zirconium, vanadium, molybdenum, manganese, tungsten, cobalt, nickel, bismuth, tin, antimony, lead, germanium, and mixtures thereof.

DETAILED DESCRIPTION OF THE INVENTION

The amino alcohols which are useful as starting materials in the process of the present invention are known to those skilled in the art. When $R^1$ and $R^2$ are both hydrogen, the amino alcohol is monoethanolamine. When one of $R^1$ and $R^2$ is hydroxyethyl and the other group is hydrogen, the amino alcohol is diethanolamine. When both $R^1$ and $R^2$ are hydroxyethyl, the amino alcohol is triethanolamine. The resulting amino carboxylic acid salts from these starting amino alcohols would be the salts of glycine, iminodiacetic acid and nitrilotriacetic acid, respectively. Other amino alcohols include N-methylethanolamine, N,N-dimethylethanolamine, N-ethylethanolamine, N-isopropylethanolamine, N-butylethanolamine, N-nonylethanolamine, N-(2-aminoethyl)ethanolamine, N-(3-aminopropyl)ethanolamine, N,N-diethylethanolamine, N,N-dibutylethanolamine, N-methyldiethanolamine,-N-ethyldiethanolamine, N-isopropyldiethanolamine, N-butyldiethanolamine, N-ethyl,N-(2-aminoethyl)ethanolamine, N-methyl,N-(3-aminopropyl)ethanolamine, tetra(2-hydroxyethyl)ethylenediamine, and the like. Other examples of aminocarboxylic acid salts are the salts of N-methylglycine, N,N-dimethylglycine, N-ethylglycine, N-isopropylglycine, N-butylglycine, N-nonylglycine, N-(2-aminoethyl)glycine, N-3-aminopropyl) glycine, N,N-diethylglycine, N,N-dibutylglycine, N-methyliminodiacetic acid, N-ethyliminodiacetic acid, N-isopropyliminodiacetic acid, N-butyliminodiacetic acid, N-ethyl, N-(2-aminoethyl) glycine, N-methyl, N-(3-aminopropyl)glycine, ethylenediaminetetraacetic acid, etc.

$R^1$ or $R^2$ can also be a phosphonomethyl group such that the starting amino acid would be N-phosphonomethylethanolamine, and the resulting amino acid would be N-phosphonomethylglycine. If one of $R^1$ or $R^2$ were phosphonomethyl, and the other were —$CH_2CH_2OH$, the resulting amino acid would be N-phosphonomethyliminodiacetic acid, which can be converted to N-phosphonomethylglycine by any number of techniques known to those skilled in the art. If one of $R^1$ or $R^2$ were phosphonomethyl, and the other were an alkyl group, the resulting amino acid would be an N-alkyl-N-phosphonomethylglycine which could be converted to N-phosphonomethylglycine by the teachings in U.S. Pat. No. 5,068,404 to Miller and Balthazor.

The copper catalyst useful in the process of the present invention can be in the form of, for example, the nitrate, sulfate, carbonate, oxide, halide, hydroxide, and the like; in the inorganic form, or as an organic compound in the form of formate, acetate, propionate, lactate, etc. There is no limitation on its shape. Thus, examples are the catalysts prepared by oxidizing the metallic copper followed by reduction by hydrogen, the catalyst obtained by developing Raney-copper alloy in an aqueous alkaline solution, the activated copper obtained by thermal decomposition and/or reduction of copper formate or copper carbonate, etc. or these catalysts carried in alkali-resistant carriers, etc. Favored carriers are titanium oxide, zirconium oxide, silicon carbide, and the like. From the standpoint of activity in the reaction and the catalyst life a developed Raney-copper or the copper catalyst carried in zirconium oxide by the coprecipitation or impregnation is preferred.

In the present invention the copper-containing catalyst contains at least one of the metals selected from the group consisting of chromium, titanium, niobium, tantalum, zirconium, vanadium, molybdenum, manganese, tungsten, cobalt, nickel, bismuth, tin, antimony, lead and germanium. To contain the said metal in the copper catalyst the metal compound can be carried in the copper-containing catalyst by coprecipitation, impregnation or adsorption, or the addition of these metals to the Raney-copper alloy in the preparation followed by development, etc.

Raney copper catalysts can be prepared by techniques known to those skilled in the art from alloys containing copper and aluminum, and thereafter, the aluminum is leached from the alloy with an aqueous alkali metal hydroxide to provide an activated Raney copper. The activated Raney copper can then be treated with a nitrate, sulfate or other salt of the elements listed above, but it is preferred to incorporate the above elements into the copper aluminum alloy during the preparation of the Raney copper to obtain a catalyst with greater stability. Of the above elements, vanadium, chromium, molybdenum, and mixtures of chromium and molybdenum are preferred.

The amount of added element in the copper catalyst can vary within wide limits. Improved results for the conversion of an amino alcohol to an amino acid can be seen with as little as 10 parts per million added element in the copper. As an upper limit, the copper can contain up to about 50,000 parts per million added element, and the copper can even contain higher levels, although such higher levels do not provide significantly improved results for the conversion of the amino alcohol to the corresponding amino acid. It is preferred to use a copper catalyst having a content of added element between about 20 and 5000 parts per million, and even more preferred is a copper catalyst having between about 50 and 5000 parts per million added element.

The amount of catalyst to be used to convert the amino alcohol to the corresponding amino acid can range between about 1% and about 70% by weight, preferably 10 to 40% by weight based on the amount of the starting amino alcohol. The catalyst can generally be used repeatedly in the reaction for a greater number of times than a copper catalyst without the added element.

The alkali metal hydroxides for use in the process of the present invention include lithium hydroxide, sodium hydroxide, potassium hydroxide, rubidium hydroxide, cesium hydroxide, and the like. The amount of the hydroxide to be used is an equivalent amount in the range of 1.0 to 2.0 equivalents relative to the hydroxyl group of the amino alcohols to be used in the reaction. The hydroxide can be in the form of flakes, powder, pellets or an aqueous solution. Because of their ready availability and ease of handling, sodium hydroxide and potassium hydroxide are preferred, and sodium hydroxide is especially preferred.

In the process of the present invention, it is only necessary to contact the amino alcohol with an alkali metal hydroxide in the presence of the copper catalyst containing about 10 parts per million to about 50,000 parts per million of the added element at a temperature between about 120° C. and 220° C., preferably between about 140° C. and about 200° C. At temperatures above about 220° C., the copper catalyst begins to lose selectivity. At temperatures below about 120° C., satisfactory results can be obtained, but the reaction is slow.

Pressure is required for the reaction to proceed at the temperatures indicated above. However, the reaction pressure is desired to be as low as possible to insure high reaction velocity. Generally, it is necessary to exceed the minimum pressure at which the reaction proceeds in the liquid phase, preferably between 5 and about 30 kg/cm², preferably in the range of 5 to 20 kg/cm². The conversion of the amino alcohol to the corresponding salt of the amino acid proceeds with the liberation of hydrogen, which should be vented with care from the reaction vessel.

The invention is further illustrated by, but not limited to, the following examples:

EXAMPLE 1

This example illustrates the results that are obtained using a Raney copper catalyst without chromium.

Into a 300 ml nickel autoclave equipped with a stirrer was charged diethanolamine (62.5 g, 0.59 mol.) water (60 ml) and a 50% aqueous solution of sodium hydroxide (50 g NaOH, 1.25 mol.) Then, a Raney copper catalyst (12.4 g) was added to the autoclave. The autoclave was sealed, and heated to a temperature of 160° C. under a pressure of 9.5 Kg/cm² while stirring the liquid phase in the autoclave. Heating was continued until hydrogen gas was no longer evolved, indicating that the reaction was complete. The reaction time was recorded, and the catalyst was reused in a subsequent run. In all cases the yield of iminodiacetic acid was about 95%. The results are shown in Table 1.

TABLE 1

Reaction Times for Repeated Use of the Same Raney Copper Catalyst

| Cycle | Reaction Time (hours) |
| --- | --- |
| 1 | 4.0 |
| 2 | 5.2 |
| 3 | 4.8 |
| 4 | 5.2 |

TABLE 1-continued

Reaction Times for Repeated Use of
the Same Raney Copper Catalyst

| Cycle | Reaction Time (hours) |
|---|---|
| 5 | 5.9 |
| 6 | 6.5 |
| 7 | 7.0 |
| 8 | 7.2 |
| 9 | 8.0 |

EXAMPLE 2

This example illustrates the use of a Raney copper catalyst containing chromium according to the present invention.

The procedure of Example i was repeated except that a Raney copper catalyst containing 943 parts per million chromium was used in 25 cycles of the catalyst. The results are shown in Table 2.

TABLE 2

Reaction Times for Repeated Use of a
Chromium Promoted Raney Copper Catalyst

| Cycle | Reaction Time (hours) |
|---|---|
| 1 | 5.8 |
| 2 | 6.7 |
| 3 | 6.6 |
| 4 | 6.2 |
| 5 | 6.4 |
| 6 | 6.3 |
| 7 | 6.0 |
| 8 | 6.0 |
| 9 | 6.0 |
| 10 | 6.2 |
| 15 | 7.0 |
| 20 | 7.0 |
| 25 | 8.0 |

A comparison of the data in Table 1 and Table 2 shows that the reaction times for the Raney copper catalyst containing chromium is longer for about the first five cycles, but remains relatively steady for an additional 20 cycles. The reaction time at cycle 25 is hours, whereas a reaction of 8 hours was reached after only 9 cycles using a standard Raney copper catalyst (Table 1).

EXAMPLE 3

This example illustrates the use of a Raney copper catalyst treated with chromic nitrate prior to its first use to convert diethanolamine to the disodium salt of iminodiacetic acid according to the present invention.

Into a 50 ml beaker is placed activated Raney copper (4.13 g), water (10 ml) and chromic nitrate (0.50 g of 15 weight % $Cr(NO_3)_3$, 4,000 ppm Cr based on the total mass of copper), and the mixture is allowed to stand 15 minutes. The Raney copper and the supernatant are transferred to a 160 ml nickel autoclave along with diethanolamine (21.2 g, 0.20 mol.) water (10 ml) and a 50% aqueous solution of sodium hydroxide (19 g NaOH, 0.42 mol.). The autoclave is sealed, and heated to 160° C. under 9.5 Kg/cm$^2$ pressure while stirring the liquid phase in the autoclave. Heating is continued until hydrogen gas is no longer evolved, indicating that the reaction is complete. The reaction time is recorded and the catalyst is reused without further addition of chromium. The results are shown in Table 3.

TABLE 3

Reaction Times for Raney Copper
Catalyst Prepared by Adding Chromium Nitrate

| Cycle | Reaction Time (hours) |
|---|---|
| 1 | 4.0 |
| 2 | 3.5 |
| 3 | 3.5 |
| 4 | 3.1 |
| 5 | 2.7 |
| 6 | 2.7 |
| 7 | 2.7 |
| 8 | 2.7 |
| 9 | 2.7 |
| 10 | 2.7 |
| 11 | 3.0 |
| 12 | 2.8 |
| 13 | 3.1 |
| 14 | 3.1 |
| 15 | 3.2 |

As the data in Table 3 indicates, reaction times improve over the first 4 cycles, and then remains relatively constant, ranging from 2.7 to 3.2 hours for the remaining cycles.

EXAMPLE 4

This example illustrates the use of the Raney copper catalyst containing chromium to convert N-(2-hydroxyethyl) aminomethylphosphonic acid to N-phosphonomethylglycine.

Into a 160 ml nickel autoclave equipped with a stirrer is charged N-(2-hydroxyethyl) aminomethylphosphonic acid (16.84 g, 0.11 mol.) water (11.3 ml) and weight % potassium hydroxide (48.7 g, 0.39 mol.) and Raney copper catalyst containing 943 parts per million chromium (3.53 g). The autoclave is sealed and heated to 160° C. under a pressure of 9.5 Kg/cm$^2$ while stirring the liquid phase in the autoclave. After 1.85 hours, hydrogen evolution ceases. The yield of N-phosphonomethylglycine as its potassium salt is 98.5%.

EXAMPLE 5

This example illustrates the conversion of N-phosphonomethyl-2-oxazolidone to N-phosphonomethylglycine using a Raney copper catalyst containing chromium.

The procedure of Example 4 is repeated except that N-phosphonomethyl-2-oxazolidone made by the process described in U.S. Pat. No. 4,547,324 is used instead of N-(2-hydroxyethyl)aminomethylphosphonic acid. After 2 hours of heating, the yield of N-phosphonomethylglycine is 86.2% as determined by HPLC analysis.

EXAMPLE 6

This example illustrates the conversion of diethanolamine to disodium iminodiacetate using a Raney copper catalyst containing molybdenum.

The procedure of Example 1 was repeated except that a Raney copper catalyst containing about 500 parts per million molybdenum was used in 12 cycles of the catalyst. After each cycle 2.5 percent of the Raney copper was replaced with fresh catalyst. The results are shown in Table 4.

TABLE 4

Reaction Times for Raney Copper
Catalyst with Added Molybdenum

| Cycle | Reaction Time (hours) |
| --- | --- |
| 1 | 3.1 |
| 2 | 3.6 |
| 3 | 3.5 |
| 4 | 3.9 |
| 5 | 4.2 |
| 6 | 4.5 |
| 7 | 4.7 |
| 8 | 4.9 |
| 9 | 5.0 |
| 10 | 5.2 |
| 11 | 5.4 |
| 12 | 5.5 |

As can be seen by comparing the reaction times in Table 4 with the reaction times in Table 1, the Raney copper containing molybdenum provided faster reactions than Raney copper without the added molybdenum. In addition, there was no adverse effect on selectivity, i.e., no increased levels of unwanted byproducts.

EXAMPLE 7

The procedure of Example 6 is repeated except that the Raney copper contains about 500 ppm chromium and 500 ppm molybdenum. Substantially the same results are obtained.

EXAMPLE 8

The procedure of Example 2 is repeated in a series of tests using Raney copper containing titanium, zirconium, niobium, tantalum, manganese, tungsten, cobalt or nickel. In each of these tests the results are not as good as the results obtained in Example 2, but are better than the results obtained in Example 1.

EXAMPLE 9

This example illustrates the conversion of diethanolamine to disodium iminodiacetate using a Raney copper catalyst containing vanadium.

Diethanolamine (71 g), sodium hydroxide (59 g), water (147 g) and Raney-copper (7 g) containing 75 ppm of vanadium were placed in a one-liter autoclave. After the atmosphere in the autoclave was replaced by nitrogen gas three times, the autoclave was heated to 170° C. and at a pressure of 10 Kg/cm$^2$ until no more hydrogen was evolved. Time required for the completion of the reaction was three hours after the temperature reached 170° C. After completion of the reaction the reaction mixture was analyzed. Conversion of diethanolamine was 99.2% and selectivity to sodium iminodiacetate was 99.2%

The experiment was repeated ten times. The time required for completion of the 10th reaction was nine hours after temperature rose to 170° C. The reaction mixture was then analyzed. Conversion of diethanolamine was 99.0%, and selectivity to sodium iminodiacetate was 98.4%

EXAMPLE 10

The procedure of Example 9 was repeated except that the autoclave was heated only to 160° C. Time required for completion of the reaction was three hours after the temperature reached 160° C. After completion of the reaction, the reaction mixture was analyzed. Conversion of diethanolamine was 99.2%, and selectivity to sodium iminodiacetate was 99.3%.

To check catalytic activity in repeated reactions, the same reaction was repeated ten times. The time required for completion of the 10th reaction was eight hours after the temperature reached 160° C. The reaction mixture was removed for analysis. Conversion of diethanolamine was 99.0%, and selectivity to sodium iminodiacetate was 98.4%.

EXAMPLE 11

This Example illustrates the use of a copper/zirconium oxide catalyst.

Zirconium oxychloride octahydrate (49.6 g) and cuprous nitrate trihydrate (16.0 g) were dissolved in water (500 ml). Aqueous sodium hydroxide solution was added to this solution to precipitate the hydroxides. The precipitate was washed in water and after drying, was immersed in 10 ml of aqueous solution containing 11 mg of ammonium metavanadate. The mixture was heated to 500° C. for three hours, then reduced in a stream of hydrogen for six hours at 230° C. to prepare a copper catalyst consisting of 82 weight % zirconium oxide, 18 weight % copper and 1140 ppm of vanadian metal based on the weight of copper.

The reaction was carried out under the same conditions used in Example 10 except that, instead of the Raney copper, 16 gm of the said catalyst containing vanadium metal, copper and zirconium were used. Time required for the reaction after the system reached 160° C. was 3.5 hours. After completion of the reaction, the mixture was analyzed. Conversion of diethanolamine was 99.0% and selectivity to sodium iminodiacetate 99.0%.

The experiment was repeated under the same conditions ten times with the same catalyst. Time required for the 10th reaction was eight hours after the temperature reached 160° C. Analysis of the reaction mixture after completion of the 10th reaction showed that conversion of diethanolamine was 99.3% and selectivity to sodium iminodiacetate 98.0%.

EXAMPLE 12

This Example illustrates the conversion of monoethanolamine to sodium glycinate.

Monoethanolamine (171 g), sodium hydroxide (123 g), water (262 g) and a Raney copper catalyst (17 g) containing 75 ppm vanadium were placed in a one-liter autoclave after flushing. After replacement of the atmosphere in the autoclave by flushing the autoclave three times with nitrogen, the reaction was carried out at 160° C. under a pressure of 10 Kg/cm$^2$ until no further hydrogen was evolved. Time required for completion of the reaction was three hours after the reaction temperature reached 160° C. After completion of the reaction, the reaction mixture was removed for analysis, which showed conversion of monoethanolamine was 99.8% and selectivity to sodium glycinate was 99.5%

The reaction was repeated under the same conditions several times. Time required for completion of the 10th reaction was six hours after the temperature reached 160° C. The reaction mixture from this reaction was analyzed, and showed that conversion of monoethanolamine was 99.3% and selectivity to sodium glycinate was 98.2%.

To show the advantages of the present invention, the above procedure was repeated except that the Raney copper catalyst did not contain any vanadium. Time required for completion of the reaction was four hours after the temperature reached 160° C. After completion of the reaction, the reaction mixture was analyzed. Conversion of monoethanolamine was 99.8% and selectivity to sodium glycinate was 99.3%.

The reaction was repeated several times under the same conditions. When the reaction was repeated ten times with the same catalyst, the time required for completion of the reaction was 10 hours after the temperature reached 160° C. The reaction mixture was removed from this reaction and analyzed. Conversion of monoethanolamine was 99.3% and selectivity to sodium glycinate was 96.2%.

EXAMPLE 13

This Example will illustrate the conversion of triethanolamine to sodium nitrilotriacetate.

Triethanolamine (188 g), sodium hydroxide (105 g), water (333 g) and Raney copper catalyst (30 g) containing 75 ppm vanadium were placed in a one-liter autoclave. After flushing the autoclave three times with nitrogen, the reaction was carried at 190° C. under a pressure of 20 Kg/cm$^2$ until no more hydrogen was evolved. Time required for the reaction after the temperature reached 190° C. was seven hours. After completion of the reaction, the reaction mixture was analyzed. Conversion of triethanolamine was 99.8%, selectivity to sodium nitrilotriacetate was 95.5%, and to by-product sodium iminodiacetate, 3.5%.

The experiment was repeated several times under the same conditions. Time required for the completion of the 5th cycle was 11 hours. The reaction mixture from this 5th reaction was analyzed. Conversion of triethanolamine was 99.3%, selectivity to sodium nitrilotriacetate was 93.2% and to by-product sodium iminodiacetate, 5.0%.

The above procedure was repeated using a Raney copper catalyst which did not contain any vanadium. Time required for the completion of the reaction was 10 hours after the temperature reached 190° C. After completion of the reaction, the reaction mixture was removed for analysis. Conversion of triethanolamine was 95.0%, selectivity to sodium nitrilotriacetate was 95.0% and that of sodium iminodiacetate, 4.0%.

The experiment was repeated under the same conditions several times. Time required for the reaction on fifth repeat was 15 hours after the temperature reached 190° C. The reaction mixture from this reaction was removed for analysis. Conversion of triethanolamine was 98.5%, selectivity to sodium nitrilotriacetate was 90.5% and that of sodium iminodiacetate, 7.5%.

EXAMPLE 14

A Raney copper catalyst (14 g) containing 190 ppm bismuth, diethanolamine (71 g), sodium hydroxide (59 g), and water (147 g) were placed in a one-liter autoclave. After flushing the autoclave three times with nitrogen, the autoclave was heated to 160° C. under a pressure of 10 Kg/cm$^2$ until no more hydrogen was evolved. The time required for the reaction was 2.5 hours after the temperature reached 160° C. After the reaction, the reaction mixture was removed for analysis. Conversion of diethanolamine was 99.8% and selectivity to sodium iminodiacetate was 98.7%.

The procedure was repeated ten times. The time required for the completion of the tenth reaction was 4.5 hours after the temperature reached 160° C. The reaction mixture from the tenth reaction was analyzed. Conversion of diethanolamine was 99.0% and selectivity to sodium iminodiacetate was 98.8%.

EXAMPLE 15

This Example illustrates the use of a Raney copper catalyst containing tin.

Diethanolamine (71 g), sodium hydroxide (59 g), water (147 g) and a Raney copper catalyst (14 g) containing 310 ppm tin were placed in a one-liter capacity autoclave. After flushing the autoclave three times with nitrogen, the reaction was performed at 160° C. under a pressure of 10 Kg/cm$^2$ until no more hydrogen was evolved. The time required for the reaction was 2.5 hours after the temperature reached 160° C. After the reaction, the mixture was removed for analysis. Conversion of diethanolamine was 99.2% and the selectivity to sodium iminodiacetate was 99.0%.

To check the activity of the catalyst after repeated use, the experiment was repeated ten times under the same conditions. When the catalyst was used repeatedly for ten times, the reaction time required for the tenth reaction was 5.5 hours after the temperature reached 160° C. The resultant reaction mixture was analyzed. Conversion of diethanolamine was 99.0% and the selectivity to sodium iminodiacetate was 98.4%.

EXAMPLE 16

This Example illustrates the use of a Raney copper catalyst containing antimony.

Diethanolamine (71 g), sodium hydroxide (59 g), water (147 g) and a Raney copper catalyst (14 g) containing 200 ppm antimony were added to a one-liter autoclave. After flushing the autoclave three times with nitrogen, the reaction was performed at 160° C. under a pressure of 10 Kg/cm$^2$ until no more hydrogen gas was evolved. The time required for the completion of the reaction was 3.5 hours after the temperature reached 160° C. After the reaction, the reaction mixture was removed for analysis. Conversion of diethanolamine was 99.2% and the selectivity to sodium iminodiacetate 99.0%.

The experiment was repeated under the same conditions ten times with the same catalyst. The time required for the completion of the tenth reaction was six hours after the temperature reached 160° C. Analysis of the reaction mixture from the tenth reaction showed that the conversion of diethanolamine was 99.0% and the selectivity to sodium iminodiacetate was 98.4%.

EXAMPLE 17

This Example illustrates the use of a Raney copper catalyst containing lead to convert monoethanolamine to sodium glycinate.

Monoethanolamine (171 g), sodium hydroxide (123 g), water (262 g) and a Raney copper catalyst (17 g) containing 100 ppm lead were placed in a one-liter autoclave. After flushing the autoclave three times with nitrogen, the reaction was carried out at 160° C. under a reaction pressure of 10 Kg/cm$^2$ until no more hydrogen was evolved. The time required for the reaction was three hours after the temperature reached 160° C. After the reaction, the reaction mixture was removed for analysis which showed that the monoethanolamine conversion was 99.8%, the selectivity to sodium glycinate was 99.5% and to the byproduced sodium oxalate 0.4%.

The reaction was repeated several times with the same catalyst. When the catalyst was used ten times, the time required for completion of the reaction was 5.5 hours after the temperature reached 160° C. Analysis of the reaction mixture from this tenth reaction gave the monoethanolamine conversion of 99.3%, the selectivity to sodium glycinate was 98.5% and to the byproduced sodium oxalate 1.0%.

EXAMPLE 18

This Example illustrates the use of a Raney copper catalyst containing germanium to convert triethanolamine to sodium nitrilotriacetate.

Triethanolamine (118 g), sodium hydroxide (105 g), water (333 g) and Raney copper catalyst (30 g) containing 100 ppm of germanium were placed in a one-liter autoclave. After flushing the autoclave with nitrogen three times, the reaction was performed at 190° C. under a reaction pressure of 20 Kg/cm² until no more hydrogen was evolved. The time required for the completion of the reaction was six hours after the temperature reached 190° C. After the reaction, the reaction mixture was removed for analysis which showed that the conversion of triethanolamine was 99.8%, the selectivity to sodium nitrilotriacetate was 94.5% and to the byproduced sodium iminodiacetate, 3.0%.

To check the catalytic activity in repeated use, the reaction was repeated several times under the same conditions with the same catalyst. When the catalyst was used five times, the time required for the completion of the reaction was 10 hours after the temperature reached 190° C. Analysis of the reaction mixture from the fifth reaction showed that conversion of triethanolamine was 99.3%, the selectivity to sodium nitrilotriacetate was 93.2%, and to the byproduced sodium iminodiacetate, 5.0%.

EXAMPLE 19

Zirconium oxychloride octahydrate (44.2 g), copper nitrate trihydrate (16.0 g) and bismuth nitrate pentahydrate (4 mg) were dissolved in 500 ml water. An aqueous solution of sodium hydroxide was added to the above solution to precipitate the hydroxides. The precipitate was washed in water and dried, then heated in air at 500° C. for three hours. It was reduced in hydrogen at 230° C. for six hours to prepare the catalyst in which bismuth and copper were carried by zirconium oxide. The reaction was carried out under the same conditions as described in Example 14 except that instead of Raney copper, 16 g of the copper-containing catalyst was used which contained 205 ppm bismuth. The time required for the reaction was 3.5 hours after the temperature reached 160° C. After completion of the reaction, the reaction mixture was analyzed. Conversion of diethanolamine was 99.0% and the selectivity to sodium iminodiacetate 99.0%, and to sodium glycinate 0.8%.

To check the catalytic activity after repeated use, the reaction was repeated several times. The catalyst was used repeatedly for ten times and the time required for the completion of the reaction at the tenth reaction was 5.5 hours after the temperature reached 160° C. Analysis of the resultant reaction mixture showed that the conversion of diethanolamine was 99.3%, the selectivity to sodium iminodiacetate was 98.0% and to the byproduced sodium glycinate 1.8%.

EXAMPLE 20

Zirconium oxychloride octahydrate (44.2 g), copper nitrate trihydrate (16.0 g) and tin nitrate (4 mg) were dissolved in 500 ml of water. The hydroxides were precipitated by the addition of sodium hydroxide solution to the above solution. The precipitate was washed in water, dried and then heated in hydrogen at 230° C. for six hours to prepare the catalyst in which tin and copper were carried by zirconium oxide. The reaction was performed under the same conditions as described in Example 14 except that, instead of the Raney copper 16 g of the copper-containing catalyst containing 310 ppm tin was used. The time required for the completion of the reaction was 4.0 hours after the temperature reached 160° C. After the reaction, the reaction mixture was analyzed. Conversion of diethanolamine was 99.0%, the selectivity to sodium iminodiacetate was 98.4% and to sodium glycinate 1.0%.

To check the catalytic activity after repeated use, the reaction was carried out repeatedly with the same catalyst. When the catalyst was used ten times, the time required for the reaction was 6.5 hours after the temperature reached 160° C. Analysis of the reaction mixture showed that the conversion of diethanolamine was 99.3%, the selectivity to sodium iminodiacetate was 98.0% and to the byproduced sodium glycinate 1.8%.

Although the invention has been described in terms of specified embodiments which are set forth in considerable detail, it should be understood that this is by illustration only, since alternative embodiments and operating techniques will become apparent to those skilled in the art in view of the disclosure. For example, any number of carboxylic acids other than those described herein can be prepared by the conversion of the corresponding amino alcohol using the Raney copper catalyst containing an added element in accordance with the teachings of the present invention. Accordingly, modifications can be made without departing from the spirit of the described invention.

We claim:

1. A process to manufacture an amino carboxylic acid salt which comprises contacting an aqueous solution of an amino alcohol represented by the formula:

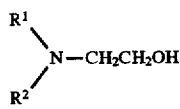

wherein $R^1$ and $R^2$ are individually selected from the group consisting of hydrogen, hydroxyethyl, —CH$_2$COOH, an alkyl group having from 1 to 18 carbon atoms, an aminoalkyl group having 2 to 3 carbon atoms, a hydroxyalkylaminoalkyl group having 2 to 3 carbon atoms, and phosphonomethyl; with an alkali metal hydroxide in the presence of an effective amount of a copper catalyst containing from about 10 parts per million to about 50,000 parts per million of an element selected from the group consisting of bismuth, tin, antimony, lead, germanium, and mixtures thereof.

2. A process of claim 1 wherein the copper catalyst contains from 50 to 5,000 parts per million of the element.

3. A process of claim 1 wherein the temperature to convert the amino alcohol to the amino acid salt is between 120° C. and 220° C.

4. A process of claim 1 wherein the copper catalyst is Raney copper.

5. A process of claim 2 wherein the copper catalyst is on an alkali resistant carrier.

6. A process of claim 8 wherein the alkali resistant carrier is zirconium oxide.

7. A process of claim 1 wherein the amino alcohol is diethanolamine.

8. A process of claim 1 wherein $R^1$ is phosphononomethyl and $R^2$ is hydrogen.

9. A process of claim 1 wherein the alkali metal hydroxide is sodium hydroxide or potassium hydroxide.

10. A process of claim 1 wherein the amount of catalyst is between 1 and 70% by weight, based on the amount of amino alcohol.

11. A process of claim 10 wherein the amount of catalyst is between 10 and 40% by weight.

* * * * *